United States Patent [19]
Pohl

[11] Patent Number: 5,409,378
[45] Date of Patent: Apr. 25, 1995

[54] APPLIANCE FOR APICOECTOMY

[76] Inventor: Yango Pohl, Schwalheimer Strasse 53, DW-6350 Bad Nauheim, Germany

[21] Appl. No.: 33,192

[22] Filed: Mar. 16, 1993

[30] Foreign Application Priority Data

Mar. 19, 1992 [DE] Germany ............... 9203684 U

[51] Int. Cl.⁶ .................... A61C 5/02; A61L 27/00
[52] U.S. Cl. ................... 433/224; 433/136; 604/304
[58] Field of Search ............ 433/136, 224; 604/304, 604/358.2, 397, 400

[56] References Cited

U.S. PATENT DOCUMENTS

| | | | |
|---|---|---|---|
| 1,649,508 | 11/1927 | Carmichael | 433/224 |
| 3,468,030 | 9/1969 | Peyser et al. | 433/136 |
| 3,857,394 | 12/1974 | Alemany | 604/285 |
| 4,372,314 | 2/1983 | Wall | 433/136 |

OTHER PUBLICATIONS

Kirschner, "Atlas der chirurgischen Zahnerhaltung", Munich/Vienna 1987, pp. 130–135.
Wilstermann, "Der retrograde Wurzelkanalverschluss mit Goldent", Deutsche Zahnärztliche Zeitschrift 29 (1974), pp. 759–760.

*Primary Examiner*—Paul J. Hirsch
*Attorney, Agent, or Firm*—Flynn, Thiel, Boutell & Tanis

[57] ABSTRACT

In apicoectomies, which are carried out after reaming out a bone cavity, treatment of a root is very often necessary. The corresponding fillings must be dry, and thus material separation of the exposed bone surface from the resection area is necessary so that no blood can enter the root region to be filled and, on the other hand, solid particles and any reagents which are necessary (for example for root canal irrigations) are unable to contact the bone cavity. An appliance is provided to allow complete lining of the bone cavity and to separate the latter materially from the root region to be filled. The lining has two layers of different and complementary function. The lining is pushed into the bone cavity using a suitable tool and, at the same time, is shaped to the surface of the cavity.

28 Claims, 4 Drawing Sheets

APPLIANCE FOR APICOECTOMY

FIELD OF THE INVENTION

The invention relates to an appliance for material separation (sealing) of the surface of a bone cavity, which is exposed during apicoectomy above the root apex of a root of a tooth, from the resection area on the root of the tooth and from the exposed root canal and a root cavity produced at the end of the canal for closing it on the side of the bone cavity, in particular during an irrigation and filling of the root canal and of the root cavity.

BACKGROUND OF THE INVENTION

The process for such an apicoectomy is described in detail by Kirschnet, "Atlas der chirurgischen Zahnerhaltung", Munich/Vienna 1987, page 130 to page 135. It entails, after the mucoperiosteum has been lifted, removing as much bone substance from the vicinity of the root apex to be resected as is necessary for performing the operation. The resulting bone cavity has a characteristic spatial shape corresponding to the root apex. After about 20% of the total length of the root has been resected, in most cases a retrograde root canal cavity is produced, and this must be filled just like the root canal itself. In this case, it is possible to insert a pin into the root canal so that only a little filling material is used.

Intraoperative root fillings require that the root canal be irrigated with highly reactive reagents such as 3% strength $H_2O_2$, 5% strength NaOCl, alcohol, etc. These irrigations emerge at the area of resection and are aspirated there, but it is not possible to avoid having a portion of the irrigations enter the bone cavity. In the case of retrograde filling, which is sometimes needed, it is also necessary to prepare the root cavity with highly reactive reagents, for example 40% strength citric acid. In this case as well, it is often unavoidable that liquid enters the bone cavity. On the other hand, the fillings have to be introduced into a dry root cavity or a completely dry root canal, and must be able to harden for a considerable time without liquid entering. Since the fillings must be introduced in excess, it is also often unavoidable that, because of the consistency of these fillings, a portion thereof enters the bone cavity and must be laboriously removed therefrom.

Oozing blood emerges from the surface adjoining the bone cavity and prevents drying both of the root cavity and of the root canal before introduction of the fillings, and contaminates the filling materials in their hardening phase.

For it to be possible, nevertheless, to carry out a satisfactory apicoectomy, it is necessary either to pack the root cavity tightly with gauze, to administer reagents which stop the bleeding due to a vasoconstrictor or astringent action, or to line the bone cavity with bone wax. In this case, it is not advantageous to administer epinephrine or the like, because of the long exposure time, the uncertain onset of its action, the uncertain duration of its action, and its hazardous side effects, especially since renewed bleeding may occur at each irrigation of the bone cavity between times. Although covering the bone surface with the aid of bone wax, which must be carried out with the bone cavity as dry as possible (after administration of hemostatic reagents), prevents further emergence of blood, it has the disadvantage that the wax particles must be removed again after the operation, which requires troublesome manipulation.

In order to eliminate these deficiencies, it has already been disclosed by Wilstermann, "Der retrograde Wurzelkanalverschluß mit Goldent", Deutsche Zahnärztliche Zeitschrift 29 (1974), pages 759 to 760, to place over the exposed root cross-section the ring-shaped loop of a ring-shaped instrument provided with a handle, which loop separates the area of resection from the surrounding retrogradely prepared bone cavity to such an extent that the root cavity and the root canal remain dry. In this case, however, a viewing restriction for the surgeon is unavoidable, and access to the area of resection is also restricted. In addition, this ring-shaped instrument has to be held throughout the treatment time. Obviously, however, this considerably impedes the work for the surgeon.

An object of the invention is therefore to provide an appliance of the type mentioned above, which remains in situ throughout the operation without having to be held, which allows clear viewing and free access to the resected area of the root apex and to the root cavity or the root canal, which can be produced easily and at low cost, and which can be introduced into the bone cavity and can be adapted in a simple manner to the particular spatial shape thereof.

SUMMARY OF THE INVENTION

This object is achieved according to the invention by the appliance being a relatively thin-wall lining which almost completely covers the surface of the bone cavity, the lining being capable of easy plastic deformation and being adaptable with the application of minimal force to the spatial shape of the surface but, on the other hand, having a residual elasticity of a magnitude sufficient to retain it in the bone cavity with a small initial tension, the lining having on its side facing the surface of the bone cavity a hemostatic and/or liquid-absorbent material.

The appliance according to the invention achieves in a surprisingly simple manner the object which has been outlined. A lining of this type can conveniently be adapted to all spatial shapes which can occur, either by various punches having respective shapes, by an elastic intermediate layer, or by manual shaping outside the bone cavity, especially when the latter is very large and the use of a punch is inconvenient. The punch is advantageously designed with thin walls, so that the root canal is easily visible on introduction of the lining into the bone cavity. Complete material separation of the surrounding bone material from the root of the tooth is now ensured, it being possible for the lining to be inserted into the bone cavity as soon as the latter is produced, and to remain therein without problems until the root filling is hardened and the operation is complete. It does not hinder the manipulations which are required, nor interfere with visual inspection thereof. The layers can without a problem have compositions which ensure that no particles can be torn out and remain in the bone cavity. The blood which emerges in the region between the lining and the bone tissue and which also coagulates there contributes to improving the adhesion of the lining. The lining itself can be produced in large numbers at very low cost, especially as a flat-web blank, and can be processed on site to an appropriate fit using scissors or the like. Emergence of blood is reliably prevented, even in the region of the bone area adjoining the area of resection, when the slightly plastic, hemostatic and/or liquid-absorbing layer is drawn over the edges of the layer responsible for the shape, so that the corner spaces are also sealed.

BRIEF DESCRIPTION OF THE DRAWINGS

The invention is explained in detail hereinafter by means of an exemplary embodiment shown in the drawings, in which.

DETAILED DESCRIPTION

Figure 1:
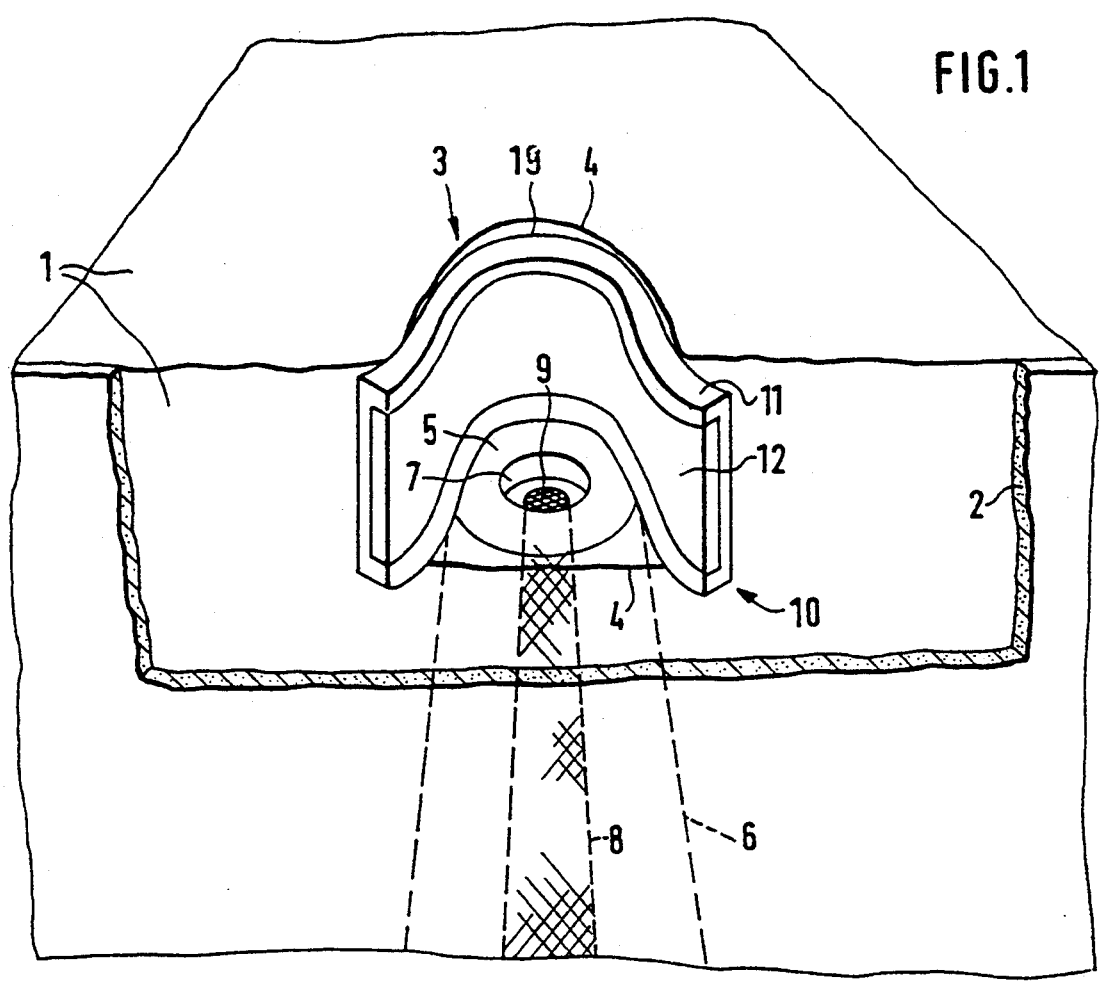
FIG. 1, 1a is a diagrammatic fragmentary perspective view showing a root apex of a root of a tooth which has been exposed and resected through an artificially produced bone cavity, and showing an appliance according to the invention which is inserted in this region.
Figure 1A:
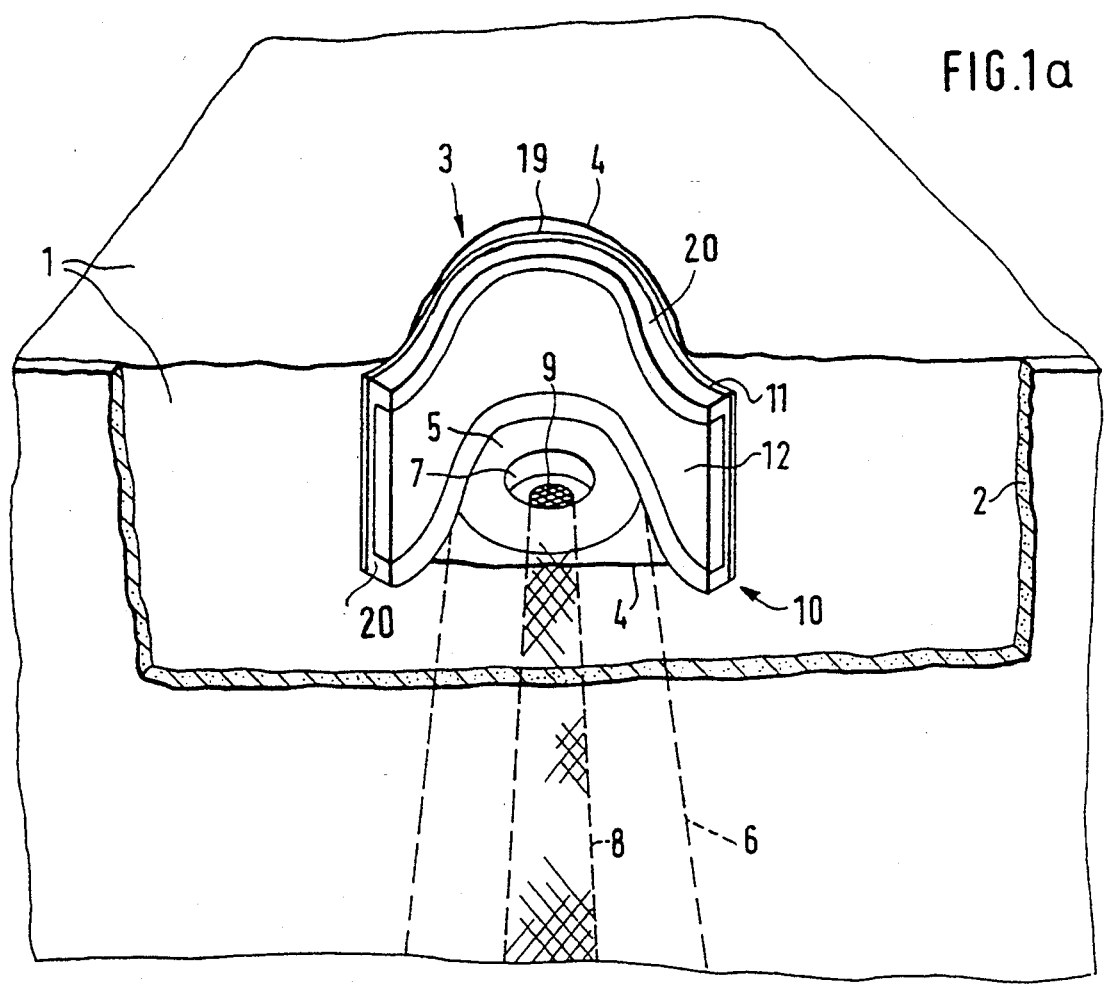
Figure 4:
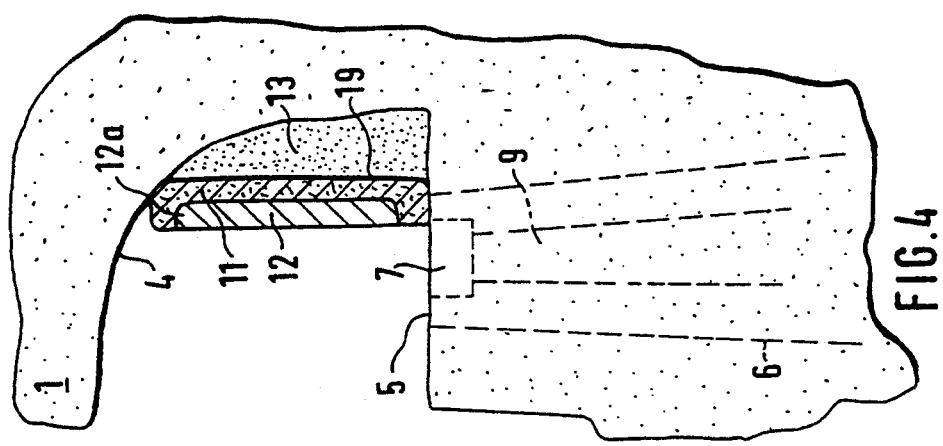
FIG. 4 is a sectional view taken along the line 4—4 in FIG. 2.
Figure 3:
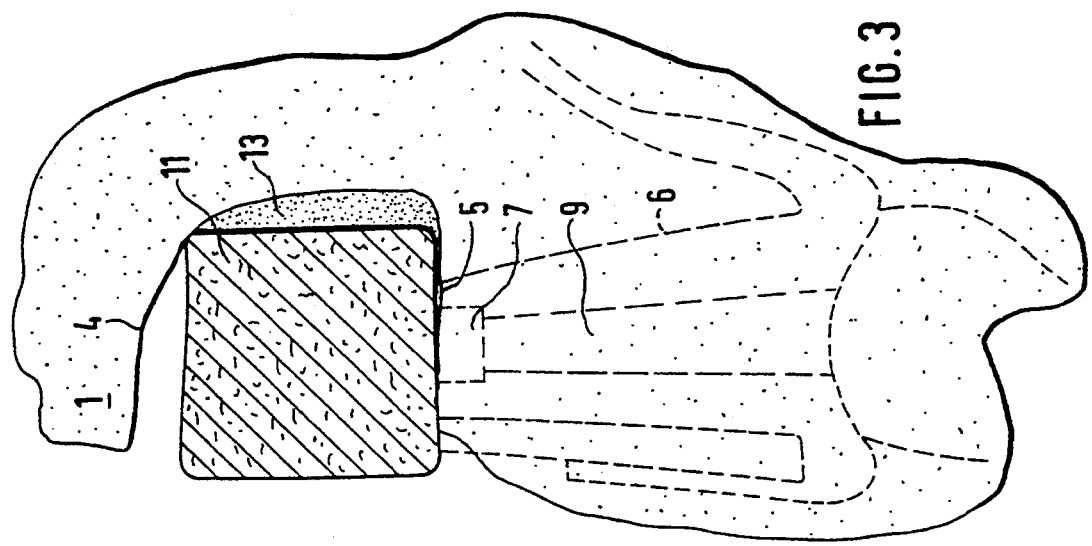
FIG. 3 is a sectional view taken along the line 3—3 in FIG. 2.
Figure 2:
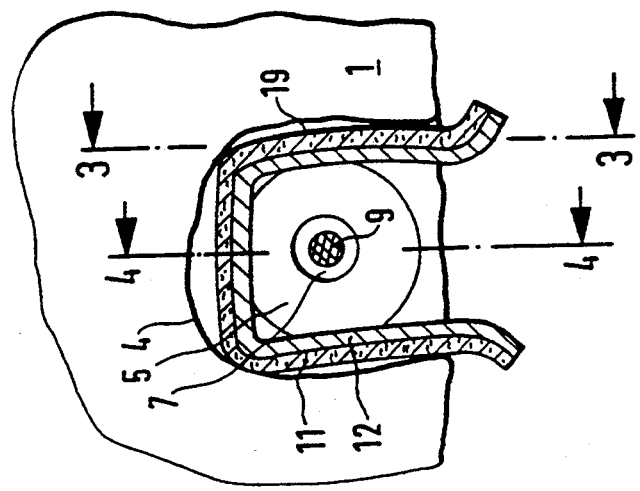
FIG. 2 is a top view of the subject matter of FIG. 1.

FIG. 1 is a diagrammatic view showing the area of a jawbone in the region of a resected root apex. In this case, the adjoining mucoperiosteal flap has been cut away from the bone 1 to such an extent that the region of operation is exposed. The lifted flap itself is omitted from the drawing, but the relevant incision site 2 is evident. A bone cavity 3 has been produced in the bone 1, and its cut surface 4 is evident in FIG. 1. The shape of the bone cavity 3 is clear, in particular, from FIGS. 2 to 4. The apicoectomy has already been performed in FIG. 1, so that a resection area 5 is visible. A root cavity 7, which is produced in the dentine of the root 6 of the tooth, is provided for retrograde filling. The root canal 8 is, in FIG. 1, already filled with a root filling material 9. A lining 10 according to the invention, which is composed of an outer layer 11 and an inner layer 12, is located in the bone cavity 3. In the top view in FIG. 2, and in the enlarged sectional views of FIGS. 3 and 4, which are rotated by 90°, the details of the lining are even more evident. Moreover, in FIG. 4 it can also be seen that the layer 11 nearest the bone has its edges curling around the edges 12a of the second layer 12 which faces the cavity. According to the invention, layer 11 is very easily plasticized, as a result of which satisfactory sealing between the bone cavity 3 and the surface 4 of the bone 1 takes place, especially in the region of the resection area 5. Blood 13, which emerges at the regions of the surface 4 not directly covered by the layer 11, coagulates (FIGS. 3 and 4) and ensures that no further blood can emerge from the incised bone 1 and interfere with the continuation of the operation.

Figures 5, 6, 7:
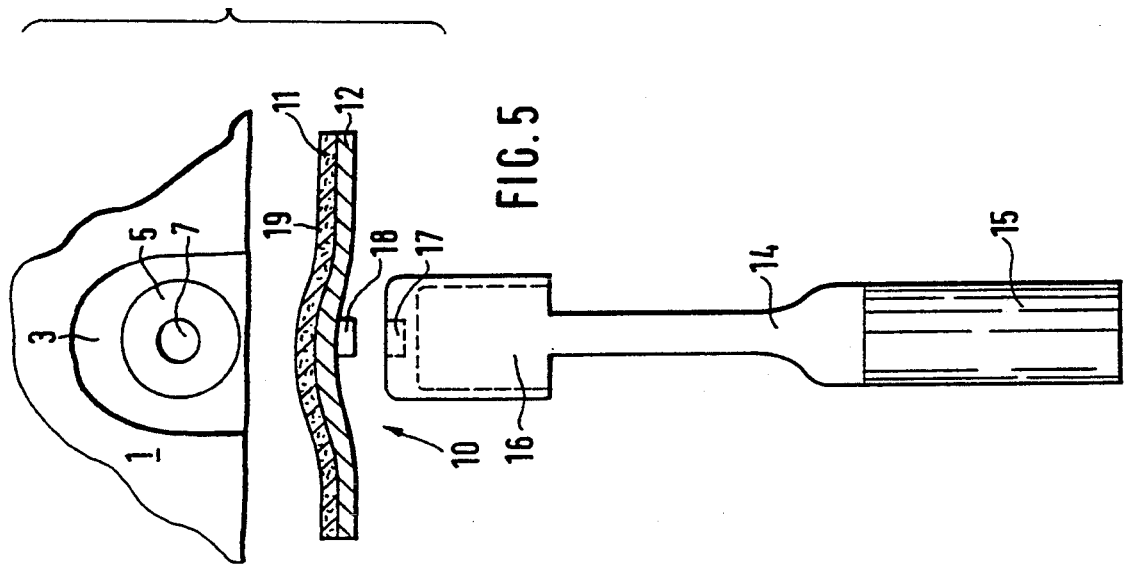
FIG. 5 is a view similar to FIG. 2 but before introduction of the appliance according to the invention.
FIG. 6 is a view similar to FIG. 5, but depicting the introduction of the appliance.
FIG. 7 is a view similar to FIG. 4 but showing an alternative embodiment of the appliance according to the invention.

FIGS. 5 and 6 show, in a highly simplified form, how the lining 10 in a blank or flat form can be pushed manually with the aid of a tamper 14 into the bone cavity 3, during which the lining 10 is reshaped into the final shape conforming to the cavity. The tamper 14 has, apart from a handle 15, a punch 16 which forms the actual tool for reshaping the blank lining 10. As evident from FIG. 5, the punch 16 undergoes positive connection to the lining 10, in this case through engagement of a recess 17 in the punch 16 with a peg 18 provided on the lining 10 on the side thereof having the layer 12. Positive connection between the lining 10 or its layer 12 and the punch 16 can be effected in a variety of ways, another example of which is shown in FIG. 7. In FIG. 7, several pairs of cooperating recesses 17 and pegs 18 are provided. Instead of this, it is also possible to use strips, or annular positive connections.

In place of the deformation (FIGS. 5 to 7) of the lining 10 with the aid of a tamper 14 or punch 16, it is also possible, especially when the bone cavity 3 is very large and, for example, embraces the region of the roots 6 of several teeth, to manually shape a lining 10 of this type outside the mouth so that it is approximately adapted to the bone cavity. After making any corrections which are necessary, the lining 10 can be used in this form in a manner appropriate for the function.

The layer 11 should undergo plastic deformation very easily, and should be hemostatic and/or liquid-absorbent, especially on its side 19 facing the surface 4 of the bone cavity 3. It is expediently composed of regenerated, oxidized cellulose or natural bovine collagen or thrombin. On the other hand, an appropriate metallic material or plastic which is, where appropriate, chosen to be hardenable, is used for the layer 12. It is essential that this layer 12 retains, after its deformation, a residual elasticity of a magnitude sufficient for the lining 10 to be held fast in the bone cavity 3 with an initial tension which, although slight, is sufficient that the surgeon can "forget" about the lining after its positioning by the surgeon. The two layers 11 and 12 are firmly connected together, for example by bonding with fibrin.

It is also possible to provide, between the layers 11 and 12, an intermediate layer 20 which is composed of an elastic plastic material and is designed to be sufficiently thick that the relatively thin layer 11 adapts better to the surface 4 and, where appropriate, compensates for roughness present there. It is, of course, necessary for all materials used to be sterilizable. It has been found that a thickness of 0.5 to 1.0 mm is optimal for the lining 10 for the purpose of application.

Although particular preferred embodiments of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an appliance for sealing of the surface of a bone cavity, which is exposed during apicoectomy above the root apex of a root of a tooth, from the resection area on the root of the tooth and from the exposed root canal and a root cavity produced at the end of the canal for closing it on the side of the bone cavity, in particular during an irrigation and filling of the root canal and the root cavity, the improvement comprising wherein the appliance includes a relatively thin-wall lining which almost completely covers the surface of the bone cavity, the lining being capable of easy plastic deformation and being adaptable with the application of minimal force to the spatial shape of the bone cavity surface but, on the other hand, having a residual elasticity of a sufficient magnitude so that it is retained in the bone cavity with a small initial tension, the lining having on a full surface of its side facing the surface of the bone cavity at least one of a hemostatic material and a liquid-absorbent material.

2. An appliance as claimed in claim 1, wherein the lining is fabricated as a flat blank and is shaped to conform to the bone cavity as it is inserted by a punch having the spatial shape of the cavity and having a thin wall construction.

3. An appliance as claimed in claim 1, wherein the lining is fabricated as a flat blank and is manually shaped outside the bone cavity to approximately conform to the spatial shape of the bone cavity.

4. An appliance as claimed in claim 1, wherein the lining has a plurality of layers.

5. An appliance as claimed in claim 4, wherein the lining has inner and outer layers which are firmly connected together.

6. An appliance as claimed in claim 5, wherein said outer layer is said hemostatic material and is very easily plasticizable, and said inner layer carries said outer layer and is likewise plasticizable in response to a deformation force but retains a certain residual elasticity.

7. An appliance as claimed in claim 1, wherein the lining is impassable to solid and liquid materials.

8. An appliance as claimed in claim 1, wherein an elastic intermediate layer which is sufficiently thick to compensate for roughness of the surface of the bone cavity is provided between an outer layer and an inner layer, at least in a partial region.

9. An appliance as claimed in claim 8, wherein at least one of the inner layer and the intermediate layer is made impassable to solid and liquid materials.

10. An appliance as claimed in claim 1, wherein the thickness of the lining is between 0.5 and 1.0 mm.

11. An appliance as claimed in claim 1, wherein the lining is composed of sterilizable material.

12. An appliance as claimed in claim 8, wherein the outer layer curls around edges of the intermediate layer, at least along part of the edges.

13. An appliance as claimed in claim 5, wherein said outer layer is composed of regenerated oxidized cellulose.

14. An appliance as claimed in claim 5, wherein said inner layer is composed of metal.

15. An appliance as claimed in claim 2, wherein the punch is positively coupled to the lining during the insertion of the lining.

16. In an apparatus which includes separation means for sealing of the surface of a bone cavity, which is exposed during apicoectomy above the root apex of a root of a tooth, from the resection area on the root of the tooth and from the exposed root canal and a root cavity produced at the end of the canal for closing it on the side of the bone cavity, in particular during an irrigation and filling of the root canal and the root cavity, the improvement comprising wherein said separation means includes a relatively thin-wall lining which almost completely covers the surface of the bone cavity, the lining being capable of plastic deformation and being adaptable with the application of minimal force to the final spatial shape of the bone cavity surface but, on the other hand, having a residual elasticity of a sufficient magnitude so that it can be retained in the bone cavity with a small initial tension, the lining having on a full surface of its side facing the surface of the bone cavity at least one of a hemostatic material and a liquid-absorbent material.

17. An apparatus as claimed in claim 16, wherein the lining is fabricated as a flat blank and is preshaped before insertion into the bone cavity in such a way that it approximately conforms to the spatial shape of the bone cavity.

18. An appliance as claimed in claim 5, wherein said outer layer is liquid-absorbing and is very easily plasticizable, and said inner layer carries said outer layer and is likewise plasticizable in response to a deformation force but retains a certain residual elasticity.

19. An appliance as claimed in claim 5, wherein said outer layer is composed of natural bovine collagen.

20. An appliance as claimed in claim 5, wherein said outer layer is composed of thrombin.

21. An appliance as claimed in claim 5, wherein said inner layer is composed of plastic.

22. An appliance as claimed in claim 8, wherein the outer layer curls around edges of the inner layer, at least along part of the edges.

23. An appliance as claimed in claim 1, wherein a plastic intermediate layer which is sufficiently thick to compensate for roughness of the surface of the bone cavity is provided between an outer layer and an inner layer, at least in a partial region.

24. An appliance as claimed in claim 23, wherein at least one of the inner layer and the intermediate layer is made impassable to solid and liquid materials.

25. An appliance as claimed in claim 23, wherein the outer layer curls around edges of the intermediate layer, at least along part of the edges.

26. An appliance as claimed in claim 23, wherein the outer layer curls around edges of the inner layer, at least along part of the edges.

27. A method of performing apicoectomy on a tooth, comprising the steps of: creating a cavity in a tooth above an apex of a root of the tooth; and sealing a surface of the tooth within said cavity, said sealing step including the step of inserting into said cavity in said tooth a relatively thin wall lining which has on a side facing the surface at least one of a hemostatic material and a liquid-absorbent material, which is capable of plastic deformation and is adaptable with the application of minimal force to a final spacial shape of the surface, and which has a residual elasticity of sufficient magnitude to retain said lining in the cavity with a small initial tension.

28. A method as claimed in claim 27, including prior to said inserting step the steps of fabricating said lining as a flat blank and preshaping said lining to approximately conform to the shape of said surface in said cavity.

* * * * *